United States Patent [19]

Widder et al.

[11] 4,009,139

[45] Feb. 22, 1977

[54] OPACIFYING AGENTS

[75] Inventors: Rudi Widder, Leimen; Paul Diessel, Mannheim; Dieter Distler, Mutterstadt, all of Germany

[73] Assignee: BASF Aktiengesellschaft, Ludwigshafen (Rhine), Germany

[22] Filed: May 22, 1975

[21] Appl. No.: 579,884

[30] Foreign Application Priority Data

June 24, 1974 Germany .......................... 2430301

[52] U.S. Cl. .................. 260/29.6 RW; 252/89 R; 252/DIG. 2

[51] Int. Cl.² ................ C08L 25/06; C08L 25/14; C11D 3/37

[58] Field of Search ................ 252/89, 95, DIG. 2; 260/29.6 RW

[56] References Cited

UNITED STATES PATENTS

| | | | |
|---|---|---|---|
| 3,326,807 | 6/1967 | Guest et al. .................. | 252/DIG. 2 |
| 3,393,153 | 7/1968 | Zimmerer .................. | 252/95 |
| 3,580,877 | 5/1971 | Corry et al. .................. | 260/29.6 RW |
| 3,666,680 | 5/1972 | Briggs .................. | 252/DIG. 2 |
| 3,669,892 | 6/1972 | Abler et al. .................. | 252/DIG. 2 |
| 3,862,906 | 1/1975 | Chambon et al. .................. | 252/DIG. 2 |

OTHER PUBLICATIONS

Rose, The Cond. Chem. Dict. 7th Ed. – 1966 Reinhold Publ. Co. p. 691.

*Primary Examiner*—Harris A. Pitlick
*Attorney, Agent, or Firm*—Johnston, Keil, Thompson & Shurtleff

[57] ABSTRACT

Opacifying agents for liquid detergents, cleaning agents and cosmetic compositions, obtained by free-radical emulsion polymerization of styrene or emulsion copolymerization of styrene with methacrylates or acrylates in the presence of sodium polyacrylate having a K value of 15 to 35 and sarcosides of unsaturated fatty acids, the solid polymer particles having a softening point above 90° C.

6 Claims, No Drawings

OPACIFYING AGENTS

This invention relates to opacifying agents based on polymers of styrene and prepared in a specific manner, for liquid compositions of various kinds, for example detergents, cleaning agents and cosmetic compositions.

Liquid detergents and cleaners essentially consist of clear aqueous or aqueous-alcoholic solutions of agents having a detergent or cleaning action. However, the users frequently prefer to use non-transparent compositions, i.e. liquid compositions which have been provided with opacifying agents, the reason for this being either that the appearance of such compositions is thus made more pleasing or that the opacifying agents facilitate visual metering.

Opacifying or clouding agents known hitherto include water-insoluble surface-active substances and polyoxyalkylene ethers. Other known opacifying agents are polymers and copolymers of styrene in the form of aqueous dispersions. Belgian Pat. No. 725,083 describes opacifying agents for liquid detergent and cleaner formulations, which opacifying agents consist of copolymer dispersions of styrene and acrylamide, methylolacrylamide or N-methylolmethacrylamide and up to 25% of other comonomers copolymerizable with styrene and the aforementioned comonomers.

These last named copolymers and also the opacifying agents based on polyalkylene polyethers suffer from the drawback that they form inadequately stable dispersions.

For example, anionic surfactants used as opacifying agents may form precipitates with cationic disinfectants or surface active substances. Conversely, precipitates may be formed when a cationic opacifying agent is used. Even non-ionic polyethylene oxide may, in some case, form precipitates when electrolytes are present in the solution. The same disadvantage occurs when use is made of the prior art styrene copolymers, since these are instable, particularly in the presence of strong alkalis.

It is an object of the present invention to provide a novel opacifying agent which is resistant, in particular, to electrolytes and strong alkalis and other surface-active materials.

We have found that this object is achieved if use is made of agents substantially consisting of an aqueous dispersion of a polymer or copolymer of styrene, which agents have been prepared in a specific manner and have a softening point above a specific temperature.

Our opacifying agents for liquid detergents, cleaners and cosmetic compositions and consisting of an aqueous dispersion of a polymer based on styrene and, optionally, other monomers copolymerizable with styrene are prepared by free-radical polymerization of styrene in aqueous emulsion or copolymerization of styrene with up to 50% by weight, based on the copolymer, of methacrylates or acrylates of from 1 to 5 carbon atoms per alkyl group in the presence of from 1 to 10% by weight, based on the total monomers, of sodium polyacrylate having a K value of from 15 to 35 (according to H. Fikentscher) and from 1 to 8% by weight of the sarcoside of an unsaturated carboxylic acid of from 12 to 20 carbon atoms per hydrocarbon radical, said opacifying agents having a softening point above 90° C.

Information on the K value and its determination is given in H. Fikentscher "Cellulosechemie", Vol. 13 (1932), pp. 55 et seq.

The main compound used in the preparation of the opacifying agents of the invention is styrene, which is preferably used alone but which may also be used in admixture with up to 50% by weight of an acrylate or methacrylate. In the latter case, the copolymerized alkyl esters of acrylic or methacrylic acid contain, according to the invention, from 1 to 5 carbon atoms per alkyl group. It is then preferred to use up to 20% by weight of methacrylate or acrylate. The most preferred comonomer has been found to be methyl methacrylate.

According to the invention, the polymerization mixtures contain from 1 to 10% and preferably from 2 to 6%, by weight, of sodium polyacrylate and from 1 to 8% and preferably from 2 to 5%, by weight, of sarcoside, preferably oleyl sarcoside, although sarcosides of other unsaturated fatty acids may be used provided they fall within the limits defined above. The polymerization is carried out as emulsion polymerization in the presence of compounds dissociating into or forming free radicals in conventional manner at from 60° to 100° C and at atmospheric or superatmospheric pressure.

Compounds which form or dissociate into free radicals are, for example, azoisobutyronitrile and peroxydisulfates such as potassium peroxydisulfate, hydrogen peroxides, organic peroxides such as dibenzoyl peroxide and dicumyl hydroperoxide. However, the success of the invention does not depend on the choice of any specific free radical agent.

The polymerization mixture may also contain, in minor quantities, anionic or non-ionic emulsifiers as conventionally used for the formation of a dispersion. Examples of anionic emulsifiers are alkali metal salts of relatively long chain fatty acids such as sodium palmitate, stearate or oleate, fatty alcohol sulfonates and olefin sulfonates of from 12 to 20 carbon atoms per alkyl radical, and sulfated ethoxylation products of fatty alcohols (ether sulfates), for example of $C_{12-15}$ alcohol cuts from Ziegler or oxo reactions.

Of greater importance are non-ionic emulsifiers such as ethoxylated fatty alcohols of the kind mentioned above, particularly those containing from 9 to 15 carbon atoms and mixtures thereof. Particularly suitable are oxo alcohols of the $C_{9-11}$ or $C_{12-15}$ cut which have been ethoxylated by a factor of from 3 to 20. The most important representatives are ethoxylated alkyl phenols, preferably octyl, nonyl or dodecyl phenol, which contain from 5 to 20 and preferably from 7 to 16 oxyethyl groups.

The above emulsifiers are not necessary for the purposes of the invention, but their presence in minor quantities is not detrimental to the efficiency of the compositions.

Polymerization leads to coarse dispersions in which the particle sizes are from 0.2 to 1 $\mu$m, which dispersed particles have a softening temperature above 90° C and preferably above 95° C. Such particle sizes are achieved because the polymer mixture is required to contain, apart from sodium polyacrylate and the sarcoside defined above, either no or only very small amounts (less than 0.5%) of the aforementioned other emulsifiers.

Polymerization carried out as defined above provides dispersions having solids contents of from 30 to 50% by weight of solid polymerized particles. These dispersions are added to detergents, cleaning agents and cosmetic compositions, referred to below as detergent solutions. By "detergent solutions" we mean compositions containing the detergents stated below as solvents in which are dissolved conventional detergent, cleaning or cosmetic additives.

The dispersions are highly stable, in spite of their coarse particle size, and cannot be broken by adding electrolytes or any kind of surface-active agent. Advantageously, the detergent solutions contain from 0.01 to 5% by weight of the opacifying agents of the invention, based on the weight of the total liquid composition.

As examples of detergents which may be mixed, in aqueous solution, with the opacifying agents, mention may be made of alkyl sulfonates, alkenyl sulfonates, hydroxyalkane sulfonates, alkylaryl sulfonates, alkylbenzimidazole sulfonates, sulfosuccinates and fatty acid condensates such as alkylmethyltaurides, fatty acid protein condensates, fatty acid alkanol amide sulfonates, fatty acid esters of hydroxyalkyl sulfonates and polyhydroxy compounds such as are derived from sugar and derivatives thereof and glycerol, sulfates of fatty alcohols and fatty acid amide ethoxylates, adducts (monoadducts or polyadducts) of alkylene oxides to fatty alcohols, alkylphenols, fatty acids, amines, mercaptans, sulfonamides and carboamides, black polymers of ethylene and propylene oxide, and optionally other alkylene oxides which may also be terminally esterified with fatty acid, or, preferably, mixtures thereof.

The type of detergent used has no appreciable influence on the action of the opacifying agent. Furthermore, our opacifying agents are completely compatible with other components of cleaning agents such as gelating agents, thickeners, hydrotropic agents (urea), tinting dyes, odorants and perfumes.

Examples of liquid compositions in which clouding may be desired are detergents and cleaners for domestic, professional and industrial use and cosmetic compositions such as foam-bath concentrates and shampoos.

The following Examples describe recipes which may contain the clouding agents of the invention.

EXAMPLE 1

A foam-bath composition contains the following ingredients, based on the weight of the composition (calculated on 100% of water): 25% of a $C_{12-15}$ alcohol ether sulfate (3 ethylene oxide groups), 0.5% of coconut oil acid diethanolamide, 0.5% of sodium chloride, 0.5% of a perfume oil and 1.0%, calculated as solids, of a 40% dispersion of polystyrene having a softening point of 95° C and a particle size of 0.5 $\mu$m, which dispersion contains, based on solids, 5% by weight of polyacrylate having a K value of 30 and 4% by weight of oleyl sarcoside.

If this composition is mixed not with the said polystyrene dispersion but with a conventional copolymer dispersion of 92% by weight of styrene and 8% by weight of acrylamide, as manufactured according to Example 2 of Belgian Pat. No. 725,083, flocculation occurs immediately.

EXAMPLE 2

A hair shampoo of similar nature was produced from 45% of the fatty alcohol ether sulfate described in Example 1, 1.0% of coconut oil acid diethanolamide, from 2.0 to 4.0% of sodium chloride and 1.0% of the opacifying agent described in Example 1. The remainder consisted of water, perfume, dye and other additives.

EXAMPLE 3

A washing-up liquid consists of, based on 100% of water, 18% of fatty alcohol ether sulfate as mentioned in Example 1, 2.5% of an $\alpha$-$C_{12}$ olefin sulfonate in the form of the sodium salt, 2.0% of sodium chloride and 1.0% of the opacifying agent described in Example 1. If, instead of the opacifying agent of the invention, a dispersion as described in Example 2 of Belgian Pat. No. 725,083 is added to this liquid, flocculation occurs.

EXAMPLE 4

A universal cleaner consists of 9% of the fatty alcohol ether sulfate of Example 1, 2.5% of the $\alpha$-olefin sulfonate of Example 3, 1.0% of oleic acid diethanolamide, 5.0% of tetrapotassium pyrosulfate, 7.0% of sodium cumene sulfonate, 1.0% of the opacifying agent described in Example 1 and 0.5% of concentrated 25% ammonia, based on 100% of water. If an opacifying agent of the prior art is added to this universal cleaner, flocculation occurs after about 3 hours.

EXAMPLE 5

An automobile shampoo consists of, based on 100% of water, 24% of fatty alcohol ether sulfate as described in Example 1, 3% of a nonylphenol ethoxylate containing 7 ethylene oxide groups, 6% of a nonylphenol ethoxylate containing 10 ethylene oxide groups and 1% of an opacifying agent of the invention as described in Example 1. If an opacifying agent prepared as described in Example 2 of Belgian Pat. No. 725,083 is added to this automobile shampoo, flocculation occurs within at most 3 hours.

We claim:
1. Opacifying agents for liquid detergent, cleaner and cosmetic compositions and which are stable in compositions containing detergents and electrolytes consisting essentially of an aqueous dispersion having a solids content of 30 to 50% by weight and a particle size of 0.2 to 1 $\mu$m and produced by the free radical polymerization of styrene or styrene with up to 50% by weight, based on the resultant copolymer, of an alkyl acrylate or an alkyl methacrylate respectively having 1–5 carbon atoms in the alkyl group in aqueous emulsion in the presence of 1 to 10% by weight, based on the total monomers, of sodium polyacrylate having a K value according to H. Fikentscher of from 15 to 35 and from 1 to 8% by weight of the sarcoside of an unsaturated carboxylic acid having from 12 to 20 carbon atoms in the hydrocarbon radical, the solid particles in said dispersion having a softening point of above 90° C.

2. Opacifying agents as claimed in claim 1, carried out as an emulsion polymerization of styrene alone.

3. Opacifying agents as claimed in claim 1, carried out as an emulsion copolymerization of styrene and up to 20% by weight of said alkyl acrylate or methacrylate.

4. Opacifying agents as claimed in claim 1, wherein said sarcoside is oleoyl sarcoside.

5. Opacifying agents as claimed in claim 1, wherein the polymerization is conducted in the presence of up to 0.5% by weight, based on the polymerization mixture, of another emulsifier which is non-ionic or anionic.

6. A process for the manufacture of opacifying agents for liquid detergent, cleaner and cosmetic compositions which comprises polymerizing at 60° – 100° C, styrene or styrene and up to 50% by weight, based on the resultant copolymer, of an alkyl acrylate or an alkyl methacrylate respectively having 1 to 5 carbon atoms per alkyl group in aqueous emulsion in the presence of a compound capable of forming or dissociating into free radicals and in the presence of from 1 to 10% by weight, based on the monomers, of sodium polyacrylate having a K value of from 15 to 35 according to H. Fikentscher and from 1 to 8% by weight of the sarcoside of an unsaturated fatty acid having from 12 to 20 carbon atoms per hydrocarbon radical and, optionally, up to 0.5% by weight, based on the polymerization mixture of a conventional non-ionic or anionic emulsifier.

* * * * *